United States Patent [19]

Verge et al.

[11] Patent Number: 5,800,817
[45] Date of Patent: Sep. 1, 1998

[54] PLANT EXTRACTS AND THERAPY FOR INSULIN DEFICIENCIES

[76] Inventors: Andre J. Verge, 102 Main St., Succasunna, N.J. 07876; Arthur J. Verge, Jr., 325 Pleasant Hill Rd., Flanders, N.J. 07836; Arthur J. Verge, III, 17 Middle Valley Rd., Long Valley, N.J. 07853

[21] Appl. No.: 613,620

[22] Filed: Mar. 11, 1996

[51] Int. Cl.$^6$ .................................................. A01N 65/00
[52] U.S. Cl. ........................ 424/195.1; 424/451; 424/464
[58] Field of Search ................................... 424/423, 424, 424/195.1, 451, 464

[56] References Cited

U.S. PATENT DOCUMENTS 5,279,949  1/1994  Nair ........................................ 435/123

*Primary Examiner*—Carlos A. Azpuru
*Attorney, Agent, or Firm*—M. Conrad Huffstutler

[57] ABSTRACT

Animal therapeutic compositions containing aqueous Taxus plant extracts for treatment of animal diseases including insulin deficiency diseases are disclosed. Bioactive Taxus-derived agents are recovered from plant parts by the extraction process disclosed. The therapeutic compositions and forms for administration provided may also include additive agents for flavoring, coloring, and preservation.

6 Claims, No Drawings

PLANT EXTRACTS AND THERAPY FOR INSULIN DEFICIENCIES

BACKGROUND OF THE INVENTION

1. Field of the Invention

The present invention is a product-by-process wherein the product is a liquid extract from Taxus plant tissue and the process for preparing the product includes a defined sequence of extraction, separation and dispersion steps to encompass selected bioactive materials and blend them into therapeutic formulations. One utility of the resulting bioactive therapeutic Taxus compositions is for treatment of insulin deficiency.

2. Description of Related Taxus-Extraction Publications

Many publications report that taxanes and other bioactive compounds produced in Taxus plant parts, because of their insolubility in water, must be extracted by organic solvents.

One example of such teaching is US5279949, Nair-949, issued Jan. 18, 1994, which describes a low-cost ethanol-water extraction method for ground, fresh needles and clippings from ornamental yew. This patent teaches solvent extraction of *Taxus hicksii* wherein the green color bodies are removed from the resulting ethanol extract by treatment with activated carbon; isolation of taxol and taxanes is accomplished using additional steps, i.e., ethyl acetate extraction and silica-gel chromatography. The latter procedure is designed to sequester immiscible plant lipids and to recover water-insoluble taxol and taxanes in ethyl acetate solvent.

It is also well known that animals such as deer and cattle can be killed by eating Taxus plant tissue. Presumably the only reason the bitter Taxus needles and branches would be consumed is that the animal was not able to find any other food and was starving. These animal experiences present clear teaching against the medicinal or therapeutic use of oral, water-base Taxus extracts by animals or humans.

No patent or publication can be found which teaches preparation of therapeutic extracts or prodrugs of *Taxus canadensis* plant parts by direct, single-stage extraction of plant elements in an aqueous fluid.

SUMMARY OF THE INVENTION

As is shown in the following description and examples, the present invention is a product-by-process, i.e., a therapeutic composition prepared by direct aqueous extraction of plant parts of *Taxus canadensis*. The present water-extraction process produces preparations containing Taxus bioactive components which benefit a variety of human conditions, particularly those related to: (a) inadequate amounts of secreted insulin, (b) secretion of insulin variants or molecular forms which are functionally defective or inefficient or (c) secretion of insulin which reacts with or binds with other serum components.

DESCRIPTION OF PREFERRED EMBODIMENTS

The process of the present invention includes the following stages: (a) selection of Taxus plant species for extraction, (b) propagation of selected varieties, (c) production of plant tissue for extraction, (d) harvesting of selected plant tissue, (e) processing of harvested plant parts, (f) extraction(s) of processed plant parts, and (g) post-extraction processing, blending of resulting extracts.

1.0 The Horticultural Processes, steps (a) through (d), for selection, propagation and production of selected Taxus plant tissue include the following stages:

1.1 Identification/propagation of root stock and/or plant cuttings for cultivation;

1.2 Selection of optimal soil and growth conditions including porosity, pH, degree-days to maturity, etc.;

1.3 Validation of preferred plant-protective measures such as sprays, soil treatments, etc.;

1.4 Confirmation of timing priorities for harvesting of specific plant parts such as specific time period, stage of maturity, leaf size parameters, plant-tissue coloration, hue, etc.;

1.5 Selecting the best techniques for harvesting from alternatives such as manual dippers, mowing, etc..

2.0 The Pre-Extraction Processing of plant parts and tissues prior to extraction, step (e), includes the following:

2.1 Mechanical processing such as cleaning, sizing, rolling, stressing, punching, cutting, macerating, etc;

2.2 Chemical processing such as spraying or dipping plant parts prior to mechanical processing with surfactants, acid, alkali, or other agents/environments which interact chemically;

2.3 Fluid-mechanical processing such as equilibrating plant tissue, prior to extraction, under specific fluid pressure, vacuum, or flow conditions, e.g., ultrasonic/vibration agitation in a vessel; and 2.4 Thermal/vacuum processing such as cooling, freezing, heating, plant tissue prior to extraction, in a chamber or vessel.

3.0 The Extraction Process, step (f), includes the following important features and control parameters:

3.1 Extract solutions, stages, sequential compositions, weight ratio fluid/plant tissue for each stage;

3.2 Extraction chamber: equipment design, vessel size, height/diameter ratio, materials, linings, coatings;

3.3 Extraction process controls, stages, time durations, temperatures, flow velocities;

3.4 End points, final stage determinations;

3.5 Separation of liquid extracts and bioactive components from plant residues.

4.0 Post-extraction preparation of therapeutic formulations from the resulting extract, step g, includes:

4.1 Therapeutic-extract concentrate blends for oral administration;

4.1.1 Blending selected additives for taste, color, preservation, degradation prevention, delayed-release, controlled-release, delayed-pulse-release, etc;

4.1.2 Selection of vehicles, excipients, fillers, viscosity control/gelling agents, etch 4.2 Extract concentrate(s) for topical, ophthalmic, mucosal, dermal/transdermal admin., drug-delivery devices/implants;

4.2.1 Blending selected additives for viscosity, porosity, resorption rate, coagulation prevention, film formation, controlled release, etc;

4.2.2 Selection of vehicles, excipients, fillers, surfactants, viscosity control/gelling agents, aerosol dispersants/stabilizers, liposome-formation agents, etc.

PREFERRED MODE—PROCESS AND THERAPEUTIC-FORMULATION PARAMETERS

Examples of processing and extract blending are given as examples P1 to P7. Examples of various Taxus extract therapeutic methods are given in Examples T1–T5.

PROCESS EXAMPLES

P1. Identification of Plants

Many reference books were used to collect plant identification data on various Taxus sub-species, including *Conifers;* Rushforth, KD; Facts On File, 1987 *Flora von Nord- und Mitteleuropa;* Hermann, F; G. Fischer, Stuttgart, 1956, and *Plant Anatomy;* Mauseth, J D; Cummings Press, Menlo Pk., Calif., 1988.

Typical plant parts were also examined by a specialist consultant to confirm correct identification. After careful examination of many plant characteristics, the plant used for the present extracts is confirmed to be *Taxus canadensis.* Plant parts from other Taxus sub-species including, but not limited to: *T. brevifolia, T. baccata, T. wallichiana, T. canadensis, T. chinesis, T. cuspidata,* and *T. floridana* are being extracted using the present process on an exploratory basis. Also, plant parts from these and any other Taxus wild-type species or Taxus cultivars may be mixed together with *T. canadensis* as described below for the preparation of extracts for the treatment of insulin deficiency and other diseases or conditions.

P2. Propagation of Plants

Taxus plants for extraction are cultivated in sandy-loam soil in marshy areas. The growth conditions are shaded. No special fertilizer, soil conditioning or protective plant sprays are used. Plants are spaced apart for controlled dissemination of the pollen and protected from injury due to browsing-animal species such as deer. Similarly, the plants must be protected from attack by browsing/chewing animal species. Although the plants exhibit a winter dormant period in the nothern latitudes, plant parts for extraction can be harvested any time of year. Plant-tissue cuttings are obtained by cutting the new-growth branches of diameter 3–10 mm into segments of approx. 70–150 mm length with pruning shears. The best time for harvesting plant cuttings is during the active-growth season when the foliage is green and pliable. The severed plant parts are lightly compressed together into small bundles, approx. 100–200 mm diam, and immediately placed into closed plastic bags for temporary storage. No cuttings are stored in such bags for more than 6 hours prior to extraction.

P3. Processing of Plant Parts

Processing of plant parts consists of: (a) washing to remove dirt and foreign matter and (b) chipping the branches, stems and needles into small segments which expose large interfacial area for diffusional transfer of bioactive species into the extract fluid. First, the cuttings are rinsed with a gentle water spray at approx 15–35 deg C., this step, which is done manually under continuous, careful visual inspection, removes environmental contaminants such as atmospheric dust/yeast/spores which settle upon the surface of the plant parts. The usual moisture level of living needles, stems and other plant parts is in the range of 10 wt. percent during the growth season; in the winter dormant season or under conditions of hot, dry ambient air, as-harvested plant tissue and whole parts may show moisture levels as low as 4–8 wt. %. Evaporation during handling or processing of harvested plant parts can further reduce their moisture level to 2–6 wt. %. Preservation of as-harvested plant parts by refrigeration or freeze-drying can result in moisture levels of 1–2 wt. %.

P4. Extractant Fluids

P4.1 A variety of types of treated and untreated water are used for extraction of Taxus plant parts including: chlorinated city water, filtered well water and unfiltered water drawn from a deep aquifer or artesian well. Simple screen and depth filtration procedures are used to remove dispersed and suspended solids from water. Aeration by bubbling air through a holding vessel may be used, if desired, to remove a portion of the chlorine. To reduce the bioburden of viable bacteria in the starting extract water, reverse osmosis or membrane ultrafiltration can also be used on at least a portion of the water used for extraction. Sensitive analysis methods for dissolved gases, metal ions and compounds may be used on a monthly or quarterly basis. Particular attention is paid to the presence of dissolved compounds of transition and heavy-metal elements.

P5. Additives to Extractant Fluid

P5.1 Chemical additives to the extract solution A variety of additives can be useful to increase recovery of bioactive agents from the plant parts into the fluid extracts. These agents include: (a) buffers for control of pH to the range 6–8, (b) antifoaming agents, (c) dissolved solutes which show a chemical affinity for, or a tendancy for forming complexes with, the bioactive agents, and (d) dissolved or dispersed additives such as cyclodextrin, which are capable of structurally encompassing bioactive species in the manner of chelates or clathrates.

P5.2 Biochemical Additives to the Extract Solution

In order to prepare a more concentrated or more stable extract, selected biochemical constituents may be added to the extract solution. It is thought that the function of at least some biochemical additives in the extract solution is: to precipitate color bodies, to neutralize undesired agents, and enhance the therapeutic properties of the bioactive species in the resulting extract. The following additives may be used with the extract fluid: (a) dissolved reactive gases such as oxygen, (b) floculating agents (c) trace minerals, such as iron, nickel, manganese, zinc or selenium, (d) plant fiber such as psyllium or cellulose and (e) vitamins or vitamin precursors such as vitamins A, B, or C as well as precursors such as beta carotene.

P5.3 Other Additives to the Extract Solution

Certain known physiologically-acceptable, compatible additives such as brighteners, clarifiers, soluble coloring, flavoring, aroma-taste additives may also be added to the extract fluid for the purpose of enhancing the appearance and palatability of the extract for oral formulations.

P6.0. Extraction Process

P6.1 Starting Materials/Batch Procedure

P6.1.1 Taxus plant parts, as-harvested moisture level, at room temp (18–28 deg. C.): approx 45 grams;

P6.1.2 Extractant, liquid water at room temp: approx 700 grams (container size/form selected such that all 45 grams of plant parts are completely immersed into and wet by extracting fluid). Generally, a deep, cylinder-form vessel of approx. 150 mm ID and 300 mm depth is used for a charge of 700 g fluid.

P6.2 Batch Extraction Process Parameters

The uncovered extraction vessel is brought quickly to a temperature of approx. 100 deg C. by application of high heat to the sides and bottom of the vessel; the liquid and plant parts reach a vigorous boiling action within approx. 5–10 minutes. The heat input is then controlled at a level to sustain an active rolling/boiling circulation pattern in the vessel for a time interval of approx. 10 minutes. Under these conditions of gentle boiling, the maximum temperature reached in water-vapor bubbles generated at the vessel heated surfaces should be below approx. 102 deg C. When the extraction-contact time has elapsed, the vessel is: (a) immediately covered with a close-fitting lid and removed from the source of heat and (b) allowed to cool in room air under quiescent conditions, i.e., no fans, air jets, or stirring/vibration of the vessel contents. Generally, the forces of free convection prior to a vigorous boil will produce fluid velocities in the range of 1–100 mm/sec. Under average boiling conditions, the velocities will fall in the range 2–200 mm/sec. A normative cool-down time falls in the range of 30–300 minutes depending upon the placement of the vessel. During boiling, there is a loss of extractant fluid vapor in the range of 10–200 g.

P6.3 Continuous Extraction Process Parameters

For high-volume production of the plant extracts of this invention, it is also possible to accomplish the extraction processes in a continuous-flow mode. For such an embodiment of the process, the plant cuttings are fed into a hopper at a rate large enough to maintain a reserve level. By means of reciprocating, rotary or combination-reciprocating-rotary comminution processes, the input plant parts are cut to the optimal ratio of exposed cut area to mass of the smallest plant portion; this ratio is in the range 0.1 to 50 mm 2 per 10 grams of as-harvested plant parts. The extraction vessel is sized to provide a retention time in the range of 10–1000 minutes and its heating means is thermostatically controlled to provide temperatures in the range 80–100 deg C. Make-up extract fluid and comminuted plant parts are fed into the extraction chamber in appropriate ratios to match the rates of removal of plant residues and extract. Continuous screen and depth filtering by known processes is used to separate suspended plant matter from the resulting extract P7.0 Post-Extraction Processing and Packaging P7.1 Separation of Plant Residues/Bulk-Storage Procedures After batch-type extraction, the fluid and plant parts are allowed to cool by natural convection against room air for a time of approx. 30–200 minutes. After the fluid has reached a temperature of approx. 25–35 deg C., fluid is filtered to remove dispersed solids larger than approx. 0.1 mm diam. The supernatant can be held in sealed containers at room temperature for testing of bioactivity and for further testing of parameters such as color, pH, density, surface tension, etc. When all testing steps are complete the approved extract fluid is repackaged and labeled with lot-number identification and held for blending into therapeutic formulations.

P7.2 End-Use Preparation and Packaging of Therapeutic Compositions

The present invention also provides therapeutic formulations which comprise compounds of the present invention formulated together with one or more non-toxic physiologically-acceptable carriers. The therapeutic formulations may be specially prepared for oral administration in solid or liquid form, for parenteral injection, or for rectal administration.

The therapeutic formulations of this invention can be administered to humans and other animals orally, rectally, parenterally, intracisternally, intravaginally, intraperitoneally, topically (as by powders, ointments, or drops), bucally, or as an oral or nasal spray. Further, therapeutic formulations of this invention may be prepared in transdermal and iontophoretic dosage forms. The nomenclature parenteral administration as used here denotes the following modes of administration: intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained by one or more of the following technics: (a) use of coating materials such as lecithin, (b) maintenance of the required particle size in the case of dispersions, and (c) surfactants.

Therapeutic formulations of this invention may also contain one or more adjuvants such as the following: preservatives, wetting agents, emulsifying agents, and dispersing agents. Prevention of the growth and action of adventitious microorganisms in formulations such as drops, syrups, elixirs, creams and ointments may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable therapeutic form may be brought about by the inclusion of agents which delay absorption such as aluminum monostearate and gelatin. In some cases, in order to prolong the effect of the bioactive agents, it is desirable to slow the absorption of the active agent from subcutaneous or intramuscular injection. This may be accomplished by the use of a liquid suspension of crystalline or amorphous material with poor water solubility. The rate of absorption of the active agents then depends upon their rates of dissolution which, in turn, may depend upon crystal size and crystalline form. Alternatively, delayed absorption of a parenterally administered therapeutic form is accomplished by dissolving or suspending the drug in an oil vehicle. Injectable depot forms are made by forming microencapsulated matrices of the active agent in biodegradable polymers such as polylactide-polyglycolide. Depending upon the ratio of bioactive agent to polymer and the nature of the particular polymer employed, the rate of delivery of the bioactive agent can be controlled. Examples of other biodegradable polymers include poly(orthoesters) and poly(anhydrides) depot injectable formulations are also prepared by entrapping the bioactive agents in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

THERAPY EXAMPLES

Solid dosage forms for oral administration including capsules, tablets, pills, powders, and granules can be prepared from the extracts of this invention. In such solid dosage forms, the bioactive agent is mixed with at least one inert, physiologically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof.

In the case of capsules, tablets and pills, prepared from extracts of this invention, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Optionally they may contain opacifying agents and can also be of a composition that they release the active ingredient(s) only, or preferentially, in a certain zone of the intestinal tract, optionally, in a delayed manner. Examples of embedding compositions which can be used include polymeric substances and waxes. The bioactive agents can also be in micro-encapsulated form, if appropriate, with one or more of the above-mentioned excipients.

Liquid dosage forms for oral administration include physiologically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the liquid oral formulations can also include adjuvants such as wetting agents, emulsifying and suspending agents, sweetening, flavoring, and perfuming agents.

Liquid-solid suspensions, in addition to the bioactive agents, may contain suspending agents as, for example, ethoxylated isostearyl alcohols, polyoxyethylene sorbitol and sorbitan esters, microcrystalline cellulose, aluminum metahydroxide, bentonite, agar-agar, and, tragacanth, and mixtures thereof.

Compositions for rectal or vaginal administration are preferably suppositories which can be prepared by mixing the bioactive agents of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Therapeutic formulations of the bioactive agents of the present invention can also be administered in the form of liposomes. As is known in the art, liposomes are generally derived from phospholipids or other lipid substances. Liposomes are formed by mono- or multi-lameliar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art.

Dosage forms for topical administration of a the bioactive agents of this invention include powders, sprays, ointments and inhalants. The active compound is mixed under sterile conditions with a pharmaceutically acceptable carrier and any needed preservatives, buffers, or propellants which may be required.

Opthalmic formulations, eye ointments, powders and solutions are also contemplated as being within the scope of this invention.

Actual dosage levels of active ingredients in the therapeutic formulations of this invention may be varied so as to obtain an amount of the bioactive agent(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Usual adult human dosage levels are in the range of about 10 to about 200 ml of filtered extract fluid per day. This dosage of extract amounts to approx. 20 to 200 mg of bioactive agent per kilogram of body weight per day and is administered in various forms. If desired, the effective daily dose may be divided into multiple doses for purposes of administration, e.g. two to four separate doses per day.

EXAMPLE T1

Aqueous Taxus Extracts Therapy

Typical adult subject background: Medical diagnosis of hyperglycemia or high blood sugar level at age 40 or later and no prior evidence of diabetes symptoms or complications.

Typical Taxus oral extract administration: Undiluted liquid extract, 0.1 ml per day per kg of body weight divided into 3 portions, each portion taken immediately before meals. Typical outcomes of Taxus extract therapy: Extract therapy must be carefully followed for at least 20 days to allow active agents to be reach an equilibrium level in blood, body tissues and organs. By day 20, a trend of lowering of blood glucose should be easily and repeatably detected by standard blood glucose self-testing devices.

EXAMPLE T2

Remission/restoration of beta-cell damage due to chemical agents such as STZ (streptozotocin) or alloxan by Taxus Extract Therapy.

Typical Subject: Murine animal model treated with chemical agent for inducing IDDM diabetes.

Typical oral Taxus extract outcomes: At a daily dosage level of 0.1 ml of extract per kg body weight, animals will be showing increased activity of sucrase alpha dextrinase and sucrose isomaltase as evidenced by enzymatic cleavage of the alpha 1–4 sucrose bond.

EXAMPLE T3

Effect of Taxus extract therapy on abnormal structure induced in sucrase alpha dextrinase by foreign insulin.

Typical Subject: Murine animal model with inherent susceptibility for diabetes and impaired glucose tolerance treated with both foreign insulin and Taxus extract.

Typical oral Taxus extract therapy outcomes: At a daily dosage level of 0.1 ml of extract per kg body weight in addition to a controlled insulin dose, animals will be showing: (a) normal levels of sucrase alpha dextrinase and (b) normative activity of the enzyme for cleavage of sucrose.

EXAMPLE T4

Effect of Taxus extract therapy on microtubule growth and development.

Typical Subject: Murine animal model with inherent susceptibility for diabetes and impaired glucose tolerance treated with Taxus extract at a daily dosage level of 0.1 ml of extract per kg of body weight.

Typical oral Taxus extract therapy outcomes: By day 20 of the treatment regimen, the animals will be showing a measurable shortening of microtubles. It is believed that the mode of anti-mitotic action of the Taxus extract is to decrease the concentration of tubulin required for assembly of the tubules.

EXAMPLE T5

Effect of Taxus extract therapy on mammal infected with Mengo or other picornavirus.

Typical Subject: Murine animal model with diabetes and impaired glucose tolerance resulting from infection with Mengo virus and treated with Taxus extract at a daily dosage level of 0.1 ml of extract per kg of body weight.

Typical oral Taxus extract therapy outcomes: By day 20 of the treatment regimen, the test animals will be showing a measurable improvement in insulin response.

The preceeding examples of this invention can be repeated with similar success by substituting generic or specifically-described agents or additives for those used in the examples. From the examples presented and previous descriptions one skilled in the art can easily ascertain the essential characteristics of the invention, and, wothout departing from the spirit and scope thereof, can make various changes and modifications of the invention to adapt it to various starting materials, animal class, healing usages and forms of adminstration.

We claim:

1. A non-toxic, bioactive, mammal-therapeutic composition which comprises a liquid extract of Taxus plant parts which is produced by the steps of:

(a) cultivating plants of one or more selected Taxus species, including: *T. canadensis, T. baccata, and T. brevifolia, T.T. chinesis, T. cuspidata, T. floridana;*

(b) harvesting tissue of parts of said cultivated Taxus plants including roots, stems, needles, blooms, seeds;

(c) cutting said freshly-harvested plant tissue of said cultivated Taxus species into lengths of 5–400 mm length;

(d) extracting said cut Taxus plant tissue and parts in a liquid-fluid solution containing at least 51% water for a time period of about 10 minutes at a temperature of about 98–102 deg C. wherein the ratio of freshly-harvested Taxus plant parts is about 20–400 grams per liter of water-base solution or about 20–350 grams of low-moisture Taxus plant parts per liter of water; and (e) separating solid plant residues of particle size greater than 0.05–0.2 mm diameter from the resulting liquid extract fluids by mechanical filtration, thereby yielding said extract.

2. A therapeutic Taxus extract composition as set forth in claim 1 wherein:

(a) *Taxus canadensis* is the selected species; and (b) said selected Taxus plants are timely harvested at a predetermined peak stage in their seasonal growth cycle immediately prior to said extraction step.

3. A therapeutic Taxus extract composition as set forth in claim 2 wherein compatible, physiologically-acceptable additives consisting of one or more of: clarifiers, preservatives, stabilizers, colorants, flavoring agents, surfactants and absorption enhancers are added to the extract in amounts sufficient to accomplish their intended purpose.

4. A method of treating animal conditions of insulin deficiency comprising daily oral ingestion of an effective amount of the composition of claim 3.

5. A therapeutic composition for oral ingestion comprising the Taxus extract of claim 3 wherein a physiologically-acceptable, compatible, palatability additive selected from the group consisting of: mint flavoring, sweeteners, pharmaceutical coloring agents and mixtures thereof is added to said extract in an amount of 0.1 to 5.0 wt. percent of said extract.

6. The therapeutic extract of claim 3 wherein step (e) of the process is followed by an additional clarification step (f) consisting of: ultrafiltration, centrifugation, floculation, membrane filtration and combinations thereof, to remove fine-disperse particles, colloids, vesicles and color bodies.

* * * * *